United States Patent [19]

Suzuki et al.

[11] Patent Number: 4,626,277
[45] Date of Patent: Dec. 2, 1986

[54] PLANT GROWTH REGULATOR

[75] Inventors: Akinori Suzuki; Akira Isogai, both of Chiba; Suong B. Hyeon, Urawa; Takashi Kikkawa, Houya; Shinzo Someya, Tokorozawa, all of Japan

[73] Assignee: Agro-Kanesho Co., Ltd., Tokyo, Japan

[21] Appl. No.: 741,807

[22] Filed: Jun. 6, 1985

[30] Foreign Application Priority Data

Dec. 6, 1984 [JP] Japan ................. 59-120550

[51] Int. Cl.$^4$ ........................................... A01N 37/06
[52] U.S. Cl. ............................. 71/113; 71/77; 71/79; 435/917
[58] Field of Search ............. 71/76, 77, 79, 106, 71/113; 435/917; 260/412.8, 404.8, 410.90

[56] References Cited

U.S. PATENT DOCUMENTS 3,558,434  1/1971  Herschler ................... 435/917

OTHER PUBLICATIONS

McCorkindale et al, "Biosynthesis of Canadensolide, etc.," (1978) 11th IUPAC Int'l. Symp. Chem. Nat. Prod., vol. 1, pp. 151–154.
Karanov et al, I, "Itaconic Acid and Some of Its, etc.," (1975) CA 84: 13409z (1976).
Karano et al, II, "Growth Regulating Activity and etc.," (1975) CA 88: 147305d (1978).
Nifant'ev et al, "Pentose Amidophosphites, etc.," (1981) CA 96: 181518a (1982).
Aleksandrova, "Newly Formed Humus, etc." (1970) CA 75: 34568e (1971).
Yuill, "Production of Itaconic Acid and, etc.," (1948) CA 42: 4641c (1948).
Halliwell, "Chromatographic Detection of, etc.," (1952) CA 46: 9653d (1952).

Primary Examiner—Glennon H. Hollrah
Assistant Examiner—R. Lelkes
Attorney, Agent, or Firm—Bucknam and Archer

[57] ABSTRACT

A plant growth regulator comprising, as its active component, one or more compounds selected from the group consisting of [+]-hexylitaconic acid, and the dihydro derivative and lower alkyl monoesters thereof is effective for growth regulation of plants.

1 Claim, 2 Drawing Figures

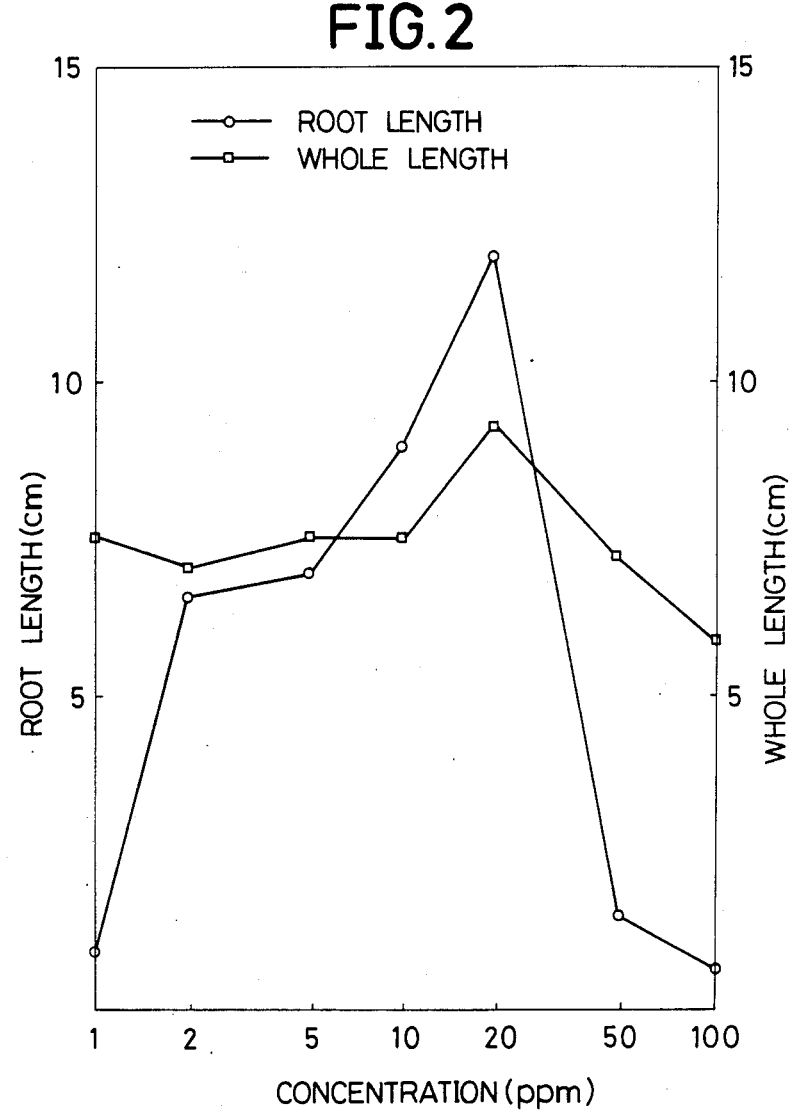

PLANT GROWTH REGULATOR

BACKGROUND OF THE INVENTION

1. Field of the Invention

The present invention relates to a novel plant growth regulator. More particularly, it relates to a plant growth regulator comprising, as its active component, one or more compounds selected from the group consisting of [+]-hexylitaconic acid, the dihydro derivative and lower alkyl monoesters thereof.

2. Brief Description of the Prior Art

Conventionally, there have been few physiologically active substances for plants that are naturally produced and actually being used at present. Among the few exceptions are gibberellic acids produced from Gibberella fujikuroi germs; cytokinin extracted from yeasts, coconut milk, fish sperms, etc.; plant auxines; ethylene gas; and the like. In particular, almost no physiologically active substances for plants produced from fungal metabolites have been known, and in the existing circumstances no physiologically active substances having effectiveness for plants corresponding to the usefulness of gibberellic acids have yet been discovered.

Especially in the field of acceleration of rooting, which is the main characteristic of the present invention, no substance produced from fungi has been discovered at all. As for the synthetic compounds, though some substances have been known such as IBA (2-indolebutyric acid), 2,4,5-T (2,4,5-trichlorophenoxy acetic acid), NAD (naphthalene acetamide), 2,4-D (2,4-dichlorophenoxy acetic acid), NAA (naphthalene acetic acid), abscisic acid and the like, the fact is that these compounds, when used for acceleration of rooting, have the deficiencies as set out below, and satisfactory uses thereof are quite limited.

(1) The use of these compounds is limited to acceleration of rooting by means of soaking the rooting parts in the chemicals. This is because these compounds lack movement within the plant, particularly basipetal movement within the plant. This can be said for all the aforementioned substances, IBA, 2,4,5,-T, NAD, 2,4-D, NAA and abscisic acid.

(2) Since the effective concentration and the critical concentration causing chemical damage are very close, some compounds cannot be used safely. The above 2,4,5-T, 2,4-D, NAD, NAA and abscisic acid are examples.

(3) Some of the compounds are problematic as regards their mamalian toxicity. The above 2,4,5-T and 2,4-D are the examples of such cases.

While the conventional chemicals have the unsolved problems as pointed out above, the naturally produced substances of the present invention have the following advantages:

(1) Their movement within the plant is great. Particularly, through foliar treatment they translocate into the lower parts of the plant and move therein to accelerate rooting. Thus they are quite convenient in use and very suitable for such purposes as growth promotion by acceleration of rooting and recovery of growth checked by environmental snags.

(2) By treating cuttings of the plant with the substances, acceleration of rooting can also be effected.

(3) Since safety to plants is quite high, they can be used safely from the early stage through the respective stages of growth.

(4) Safety for mammalia is very high.

Since the substances of the present invention make it possible to overcome the problems of the conventional chemicals, their agricultural and horticultural usefulness is remarkable.

BRIEF SUMMARY OF THE INVENTION

In the course of a series of studies for the useful plant-activating substances produced from fungal metabolites, the inventors of the present invention discovered from *Aspergillus niger* K-88 strain substances that notably accelerate rooting of plant and confirmed that the active substance thereof was [+]-hexylitaconic acid whose structure could be represented by the molecular formula $C_{11}H_{18}O_4$ or by the structural formula;

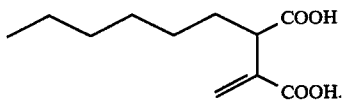

The inventors also found that the dihydro derivative and lower alkyl monoesters thereof have an excellent accelerating action on rooting and thus completed the present invention.

DETAILED DESCRIPTION OF THE INVENTION

Figure 1:
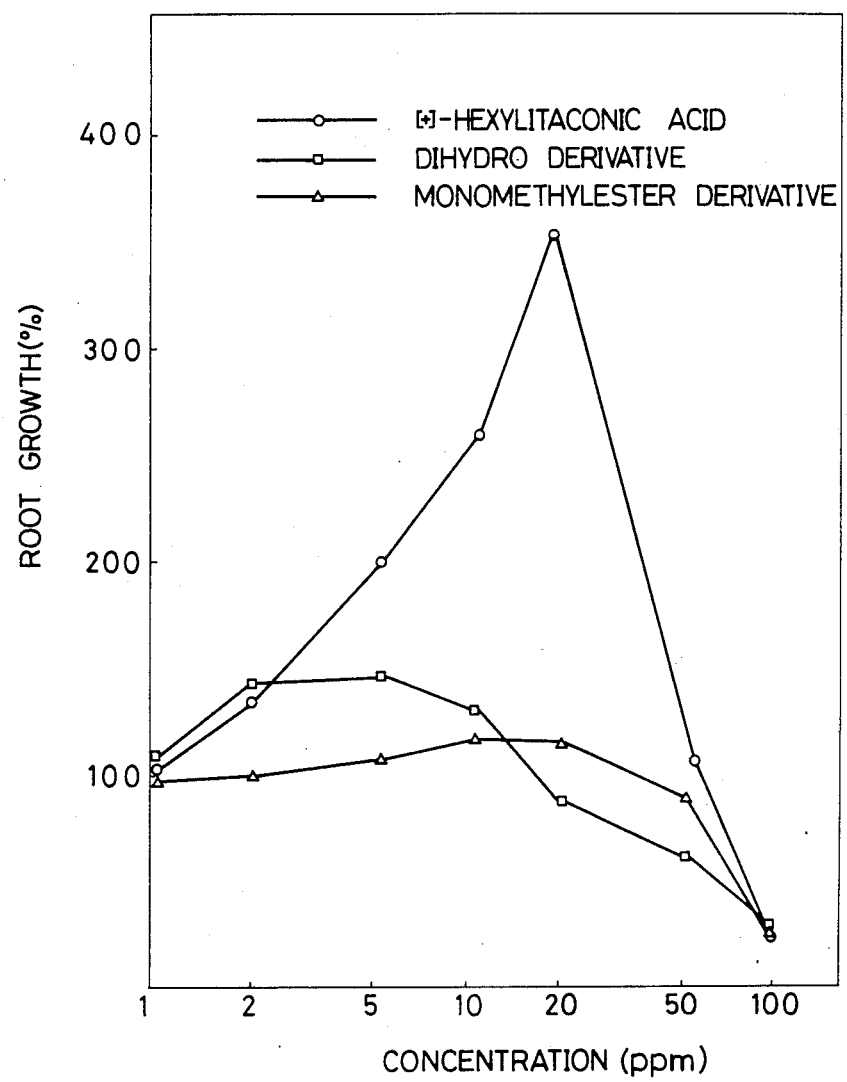

As stated above, in the course of a series of studies on useful physiologically active substance for plants produced from fungal metabolites, the inventors of the present invention discovered substances from *Aspergillus niger* K-88 strain that notably accelerate plant root length, particularly, in rice plant and lettuce. As a result of an investigation of the active substance from the purified substance from assay medium, the inventors confirmed that the substance was [+]-hexylitaconic acid whose structure could be represented by the molecular formula $C_{11}H_8O_4$ or by the structural formula;

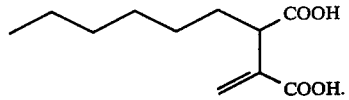

Though some reports have been made public on the syntheses of said [+]-hexylitaconic acid itself (N. S. McCorkindale, W. P. Backstock, G. A. Johnstone, T. R. Roy and J. A. Toke; refer to the 11th Iupac Int. Sump. Chem. Nat. Pro. 1, 151 (1978), none of the reports describes the circumstances under which the syntheses came to be attempted and the purposes thereof. And the separation of said [+]-hexylitaconic acid from natural products seems to have been made for the first time by the inventors of the present invention in their research. Moreover, it is quite a novel discovery made by the inventors of the present invention that said [+]-hexylitaconic acid, the dihydro derivative and the lower alkyl monoesters thereof shows a very remarkable action to accelerate rooting, which suggests their useful applicability to farm product-growing.

Next, we explain the separation and purification of said [+]-hexylitaconic acid and the synthesis of the dihydro derivative and lower alkyl monoesters thereof.

I. Separation and Purification of [+]-Hexylitaconic Acid

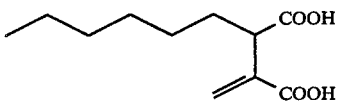

The *Aspergillus niger* K-88 strain separated from the soil of Ninomiya-cho, Kanagawa Prefecture was subjected to shaking culture in a Czapek-Dox culture medium at the temperature 26.5° C., for ten days, then 5.2 l culture filtrate (pH 2) was extracted with ethyl acetate, and the organic layer was extracted with a sodium bicarbonate solution. The aqueous solution layer was adjusted to pH 3, and after extracting with ethyl acetate, the organic layer was dried over sodium sulfate, and evaporated under reduced pressure. Thereby, 740 mg of oily acid material was obtained. The oil fraction was treated in a Wakogel C-100 column (⌀3.1×43 cm), and rendered in hexane-ethyl acetate, then the concentration of the ethyl acetate was gradually increased. The rendered solution having a hexane-ethyl ratio 6:4 was successively divided into four equal amount divisions. From the crude active material of the second division, 74 mg of the pure product was obtained by means of thin layer chromatography of Kiesel gel $F_{254}$ (hexane-ethyl acetate-acetic acid 4:6:0.1). The characteristic data were as follows:

mp 46°–47° C.; $(\alpha)D+15.3$ (c=2.0, methanol), MS m/z:

214.1225 (M+, 5%, Calculated value as $C_{11}H_{18}O_4$, 214.1195), 196.1074 (M-$H_2O$, 5%; Calculated value as $C_{11}H_{16}O_3$, 196.1034), 178.1010 (M-2$H_2O$, 5%; Calculated value as $C_{11}H_{14}O_2$, 178.0994), 169.1246 (M-COOH, 43%; Calculated value as $C_{10}H_{17}O_2$, 169.1229), 129.0117 (M-$C_6H_{13}$, 55%; Calculated value as $C_5H_5O_4$, 129.0188), 112 (M-$C_6H_{12}$-$H_2O$, 100%);

IR$\nu_{max}^{film}$ (cm$^{-1}$): 3300–2400, 1775, 1705, 1625.

$^{13}$C-NMR$\delta$ C (CDCl$_3$); 179.6 (s, C-1), 171.7 (s, C-4), 137.5 (s, C-3), 129.6 (t, C-11), 47.0 (d, C-2), 31.7 (t, C-8), 29.9 (t, C-5), 29.0 (t, C-7), 27.4 (t, C-6), 22.6 (t, C-9), 14.1 (q, C-10); δ C (CD$_3$OD): 169.4 (s, C-4), 176.9 (s, C-1).

$^1$H-NMR$\delta$ H (CDCl$_3$): 0.83 (3H, t, J=6 Hz, H-10), 1.25 (8H, br s, H-6.H-9), 1.80 (2H, m, H-5), 3.35 (1H, t, J=7 Hz, H-2), 5.80 (1H, s, H-11a), 6.40 (1H, s, H-11b), 9.6 (2H, br s, 2×COOH).

II. Synthesis of Dihydro Derivative

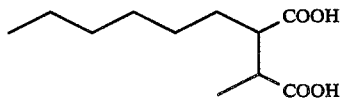

By reducing 20 mg of [+]-hexylitaconic acid in methanol by use of a platinum oxide catalyst, 20 mg of a dihydro derivative was obtained. The characteristic data thereof were as follows:

mp 109°–112° C. (Acetone-$H_2O$).

IR$\delta_{max}^{KBr}$ (cm$^{-1}$): 3400–2400, 1690.

$^{13}$C-NMR$\delta$ C (CD$_3$OD): 178.5 (s, C-4 or C-1), 177.8 (s, C-1 or C-4), 50.0 (d, C-2), 43.3 (d, C-3), 32.5 (t, C-8), 31.8 (t, C-5), 29.9 (t, C-7), 28.3 (t, C-6), 23.4 (t, C-9), 15.8 (q, C-11), 14.2 (q, C-10).

$^1$H-NMR$\delta$ H (CDCl$_3$): 0.83 (3H, t, J=6 Hz, H-10), 1.2–1.8 (13H, m, H-5.H-9, H-11), 2.7 (2H, m, H-2, H-3), 8.8 (2H, br s, 2×COOH).

III. Synthesis of Monomethyl Ester Derivative

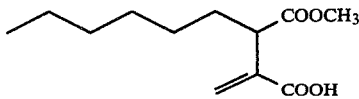

In 5% HCl-containing methanol, 20 mg of [+]-hexylitaconic acid was refluxed for one hour, and the reaction mixture was poured in water, then extracted with ethyl acetate. The ethyl acetate layer was extracted with sodium bicarbonate aqueous solution. After adjusting the water layer to have pH 3, it was re-extracted with ethyl acetate. The extract was dried over anhydrous sodium sulfate, then concentrated under reduced pressure. The concentrated residue was separated and purified by thin layer chromatography; thereby 10 mg of a monomethyl ester derivative was obtained. The characteristic data were as follows:

MS m/z: 228 (M+, $C_{12}H_{20}O_4$), 197 (M-OCH$_3$), 183 (M-COOH), 143 (M-$C_6H_{13}$), 112 (M-$C_6H_{12}$-CH$_3$OH).

IR$\nu_{max}^{film}$ (cm$^{-1}$): 3400–2400, 1775, 1740, 1700, 1625.

$^{13}$C-NMR$\delta$ C (CDCl$_3$): 173.8 (s, C-1), 171.5 (s, C-4), 138.1 (s, C-3), 129.1 (t, C-11), 52.1 (q, OCH$_3$), 46.5 (d, C-2), 31.6 (t, C-8), 31.4 (t, C-5), 29.0 (t, C-7), 27.5 (t, C-6), 22.6 (t, C-9), 14.1 (q, C-10).

$^1$H-NMR$\delta$ H (CDCl$_3$): 0.82 (3H, t, J-6 Hz), 1.2 (8H, br s), 1.8 (2H, m), 3.35 (1H, t, J=7 Hz), 3.55 (3H, s, OCH$_3$), 5.80 (1H, s), 6.40 (1H, s).

Said [+]-hexylitaconic acid and the dihydro derivative thereof remarkably accelerate rooting of rice plants, lettuce, etc., at the concentrations from 1 to 20 ppm, and at the same time promote the growth of foliar parts.

FIG. 1 shows the rooting acceleration effects on lettuce exerted by said [+]-hexylitaconic acid, the dihydro and monomethyl ester derivatives thereof at various concentrations. FIG. 2 shows the growth- and rooting-accelerating effects on paddy rice plants exerted by said [+]-hexylitaconic acid at various concentrations.

Hereinafter we describe the present invention further in detail in concrete examples. The present invention is, of course, not limited to these Examples.

EXAMPLE 1

Rooting Test on Lettuce

A sheet of filter paper having a diameter 5.5 cm was laid on a petri dish, and a definite amount of a verifying substance dissolved in acetone was added thereon. After the acetone had been evaporated, 2 ml of a Hoagland solution was added to the perti dish, whereafter seven lettuce seeds right after germination were placed thereon per dish. The treated dishes were irradiated at 3000 lux for three days, and kept at the temperature ±2° C.

Test Results

FIG. 1 shows the rooting rates obtained by the treatments with the [+]-hexylitaconic acid, the dihydro derivative and the monomethyl ester derivative thereof at the respective treating concentrations. As clearly seen from FIG. 1, it was found that all the respective substances exhibited rooting-acceleration effects at concentrations in the range of about 1 to 20 ppm, while at the higher concentrations in the range of 50 to 100 ppm, they worked to check growth.

EXAMPLE 2

Rooting Test on Paddy Rice Plant

In a test tube of a diameter 2.5 cm, a definite amount of [+]-hexylitaconic acid dissolved in acetone was added, whereafter the acetone was evaporated. To the tube, 2 ml of eight-times diluted solution of Kimura's B Liquid [The composition of the liquid was as follows:

| $(NH_4)_2SO_4$ | 18.2 mg | N | 23.0 mg |
|---|---|---|---|
| | | ($NH_4$—N | 10.2) |
| | | ($NO_3$—N | 12.8) |
| $K_2SO_4$ | 15.9 mg | $P_2O_3$ | 13.0 mg |
| $MgSO_4$ | 65.9 mg | $K_2O$ | 17.2 mg |
| $KNO_3$ | 18.5 mg | CaO | 20.5 mg |
| $Ca(NO_3)_2$ | 59.9 mg | MgO | 22.1 mg |
| $KH_2PO_4$ | 24.8 mg | | |
| Fe-citrate | 2-5 mg as $Fe_2O_3$ | | |

Refer to "Methods for Testing Farm Products, by Baba and Takahashi (under the supervision of Tokari), published by Nogyo Gijutsu Kyokai, 1959] was added. Five grains of paddy rice plant right after germination were put in each tube, and the test tubes were covered with plastic films. These tubes were irradiated at 3000 lux for seven days and kept at the temperature 30±2° C.

Test Results

FIG. 2 shows the activities of [+]-hexylitaconic acid in growth- and rooting-acceleration. As clearly seen from FIG. 2, [+]-hexylitaconic acid remarkably accelerated the rooting of the paddy rice plants at concentrations in the range of from 2 ppm to 20 ppm. On the other hand, the whole length of the overground parts of the plants (the length of the foliar parts) was increased about 20% at the concentration of 20 ppm.

EXAMPLE 3

Rooting-acceleration Test on Seedlings of Rice Plant

After spraying a 50 ppm or 25 ppm concentration of [+]-hexylitaconic acid over the foliar parts of the 10 seedlings per block of rice plant grown to the 2.5 leaf stage and cutting the root length of 2 cm, the seedlings were hydroponically cultured. Two weeks later, the number of rootings was examined. Separately, after cutting the root length of 10 seedlings of rice plant per block to 2 cm, the seedlings were hydroponically cultured in a 50 ppm or 25 ppm solution of [+]-hexylitaconic acid. Two weeks later, the number of rootings was examined.

Test Results

TABLE 1

| Number of Rootings of Seedlings of Rice Plant | | |
|---|---|---|
| Concentration of Sample (ppm) | Foliar Treatment | Soaking Treatment |
| 50 | 72 (156%) | 108 (177%) |
| 25 | 74 (160%) | 107 (175%) |
| Untreated | 46 (100%) | 61 (100%) |

As clearly shown from Table 1, very remarkable increase in the number of rootings was noted both in the foliar treatment and the soaking treatment.

We claim:

1. The method of accelerating rooting in plants which consists of treating said plants with an effective amount of [+]-hexylitaconic acid.

* * * * *